US00PP18517P2

(12) United States Plant Patent
Klemm

(10) Patent No.: US PP18,517 P2
(45) Date of Patent: Feb. 26, 2008

(54) ***OSTEOSPERMUM* PLANT NAMED 'KLEOE05524'**

(50) Latin Name: *Osteospermum ecklonis*
Varietal Denomination: KLEOE05524

(75) Inventor: Nils Klemm, Stuttgart (DE)

(73) Assignee: Klemm + Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 11/583,609

(22) Filed: Oct. 19, 2006

(51) Int. Cl.
*A01H 5/00* (2006.01)

(52) U.S. Cl. ..... Plt./360
(58) Field of Classification Search ..... Plt./360
See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Osteospermum* plant named 'KLEOE05524', characterized by its upright and compact plant habit; freely branching growth habit; early and freely flowering habit; and large daisy-type inflorescences with bright yellow-colored ray florets.

1 Drawing Sheet

Botanical designation: *Osteospermum ecklonis.*
Cultivar denomination: 'KLEOE05524'.

BACKGROUND OF THE INVENTION

The present invention relates to a new and distinct cultivar of *Osteospermum* plant, botanically known as *Osteospermum ecklonis,* and hereinafter referred to by the name 'KLEOE05524'.

The new *Osteospermum* is a product of a planned breeding program conducted by the Inventor in Stuttgart, Germany. The objective of the program is to create and develop new compact *Osteospermum* cultivars with freely branching and uniformly mounded plant habit, early and freely flowering habit and attractive inflorescence coloration.

The new *Osteospermum* originated from an open-pollination by the Inventor in 2002 of an unnamed proprietary selection of *Osteospermum ecklonis,* not patented, as the female, or seed, parent with an unknown selection of *Osteospermum ecklonis* as the male, or pollen, parent. The new *Osteospermum* was discovered and selected by the Inventor as a single flowering plant within the progeny of the stated open-pollination in a controlled environment in Stuttgart, Germany in April, 2003.

Asexual reproduction of the new *Osteospermum* by terminal cuttings in a controlled environment in Stuttgart, Germany since May, 2003, has shown that the unique features of this new *Osteospermum* are stable and reproduced true to type in successive generations.

SUMMARY OF THE INVENTION

The cultivar KLEOE05524 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'KLEOE05524'. These characteristics in combination distinguish 'KLEOE05524' as a new and distinct cultivar of *Osteospermum:*

1. Upright and compact plant habit.
2. Freely branching growth habit.
3. Early and freely flowering habit.
4. Large daisy-type inflorescences with bright yellow-colored ray florets.

In side-by-side comparisons conducted in Stuttgart, Germany, plants of the new *Osteospermum* differ from plants of the female parent selection in the following characteristics:

1. Plants of the new *Osteospermum* are more compact and uniform than plants of the female parent selection.
2. Plants of the new *Osteospermum* and the female parent selection differ in ray floret coloration.

Plants of the new *Osteospermum* can be compared to plants of the *Osteospermum* cultivar FP Sunrise, not patented. In side-by-side comparisons conducted in Stuttgart, Germany, plants of the new *Osteospermum* differed from plants of the cultivar FP Sunrise in the following characteristics:

1. Plants of the new *Osteospermum* had smaller leaves than plants of the cultivar FP Sunrise.
2. Plants of the new *Osteospermum* and the cultivar FP Sunrise differed in ray floret coloration as plants of the cultivar FP Sunrise had lighter yellow-colored ray florets.

BRIEF DESCRIPTION OF THE PHOTOGRAPH

The accompanying photograph illustrates the overall appearance of the new *Osteospermum.* This photograph shows the colors as true as it is reasonably possible to obtain in colored reproductions of this type. Colors in the photograph may differ slightly from the color values cited in the detailed botanical description which accurately describe the colors of the new *Osteospermum.* The photograph comprises a close-up view of typical flowering plants of 'KLEOE05524'.

DETAILED BOTANICAL DESCRIPTION

In the following description, color references are made to The Royal Horticultural Society Colour Chart, 1995 Edition, except where general terms of ordinary dictionary significance are used. The aforementioned photograph, following observations and measurements describe plants grown in Stuttgart, Germany during the summer in an outdoor nursery and under conditions and practices which approximate those generally used in commercial *Osteospermum* production. During the production of the plants, day temperatures ranged from 15° C. to 20° C. and night ranged from 10° C. to 15° C. Measurements and numerical values represent averages for typical flowering plants. Plants were about six months old when the photograph and description were taken.

Botanical classification: *Osteospermum ecklonis* cultivar KLEOE05524.

Parentage:

*Female, or seed, parent.*—Unnamed proprietary selection of *Osteospermum ecklonis,* not patented.

*Male, or pollen, parent.*—Unknown selection of *Osteospermum ecklonis,* not patented.

Propagation:

*Type.*—Terminal vegetative cuttings.

*Time to initiate roots, summer.*—About ten days at 25° C.

*Time to initiate roots, winter.*—About two weeks at 18° C. to 20° C.

*Time to produce a rooted cutting, summer.*—About three to four weeks at 25° C.

*Time to produce a rooted cutting, winter.*—About four to five weeks at 18° C. to 20° C.

*Root description.*—Fibrous.

*Rooting habit.*—Freely branching; dense.

Plant description:

*Plant form/growth habit.*—Upright and compact plant habit. Inflorescences positioned well above the foliar plane. Moderately vigorous growth habit.

*Plant height.*—About 33 cm to 40 cm.

*Plant diameter.*—About 30 cm to 45 cm.

*Lateral branches.*—Quantity per plant: Freely branching, about four to six lateral branches per plant. Length: About 40 cm to 44 cm. Diameter: About 1 cm. Internode length: About 0.5 cm to 2 cm. Strength: Strong. Texture: Pubescent. Color: 144B flushed with 176A.

*Foliage description.*—Arrangement: Alternate, simple. Length: About 7 cm. Width: About 2 cm. Shape: Obovate. Apex: Acute. Base: Acute. Margin: Crenate. Texture, upper and lower surfaces: Sparsely pubescent. Venation pattern: Pinnate. Color: Developing foliage, upper and lower surfaces: 144A. Fully expanded foliage, upper surface: 146A; venation, 144C. Fully expanded foliage, lower surface: 146B; venation, 144C.

Inflorescence description:

*Appearance.*—Daisy-type inflorescence form with obovate-shaped ray florets. Inflorescences positioned above the foliage, arising from leaf axils. Disc and ray florets developing acropetally on a capitulum. Inflorescences face mostly upright. Freely flowering habit; about 90 inflorescences develop over time per plant. Inflorescences persistent. Inflorescences not fragrant.

*Flowering response.*—In Germany, plants of the new *Osteospermum* flower recurrently to continuously from spring to autumn. Early flowering habit, plants being flowering about 10 to 16 weeks after planting. Inflorescences last about five to ten days on the plant.

*Inflorescence bud.*—Height: About 1.3 cm. Diameter: About 8 mm. Shape: ovate. Color: 144A.

*Inflorescence size.*—Diameter: About 5 cm. Depth (height): About 2 cm. Disc diameter: About 1.2 cm. Receptacle diameter: About 1.2 cm. Receptacle height: About 1 cm.

*Ray florets.*—Shape: Obovate. Length: About 2 cm. Width: About 1 cm. Apex: Obtuse. Base: Acute. Margin: Entire. Texture: Smooth, glabrous; velvety. Orientation: Upright. Number of ray florets per inflorescence: About 17 to 20 in a single whorl. Color: When opening, upper surface: 14A. When opening, lower surface: 14A; longitudinal stripes, 184A. Fully opened, upper surfaces: 14A; towards the base, 12A. Fully opened, lower surface: 14A; longitudinal stripes, 184A.

*Disc florets.*—Shape: Tubular; apex dentate, five-pointed. Length: About 5 mm. Diameter, apex: About 2 mm. Diameter, base: Less than 1 mm. Number of disc florets per inflorescence: About 30 to 34. Color: Immature: 9B. Mature: Apex: 9B. Mid-section: 15D. Base: 150D.

*Phyllaries.*—Quantity per inflorescence: About 19. Length: About 1.2 cm. Width: About 2 mm. Shape: Lanceolate. Apex: Acuminate. Base: Truncate. Margin: Entire. Texture, upper surface: Smooth, glabrous. Texture, lower surface: Pubescent, rough. Color, upper and lower surfaces: 146D.

*Peduncles.*—Length: About 12 cm to 15 cm. Diameter: About 2 mm. Strength: Strong. Aspect: Mostly upright. Texture: Pubescence; rough. Color: 146D.

*Reproductive organs.*—Androecium: Present on disc florets only. Anther shape: Ovate. Anther length: About 1 mm. Anther color: 93A. Pollen amount: Abundant. Pollen color: 25A. Gynoecium: Present on both ray and disc florets. Pistil length: About 2 mm. Stigma shape: Lanceolate. Stigma color: 145B. Style length: About 1 mm. Style color: Close to 83A.

*Seeds.*—Length: About 6 mm. Diameter: About 3 mm. Color: 200A.

Disease/pest resistance: Plants of the new *Osteospermum* have not been shown to be resistant to pathogens and pests common to *Osteospermums*.

Temperature tolerance: Plants of the new *Osteospermum* have been observed to tolerate temperatures ranging from about −5° C. to about 35° C.

It is claimed:

1. A new and distinct *Osteospermum* plant named 'KLEOE05524' as illustrated and described.

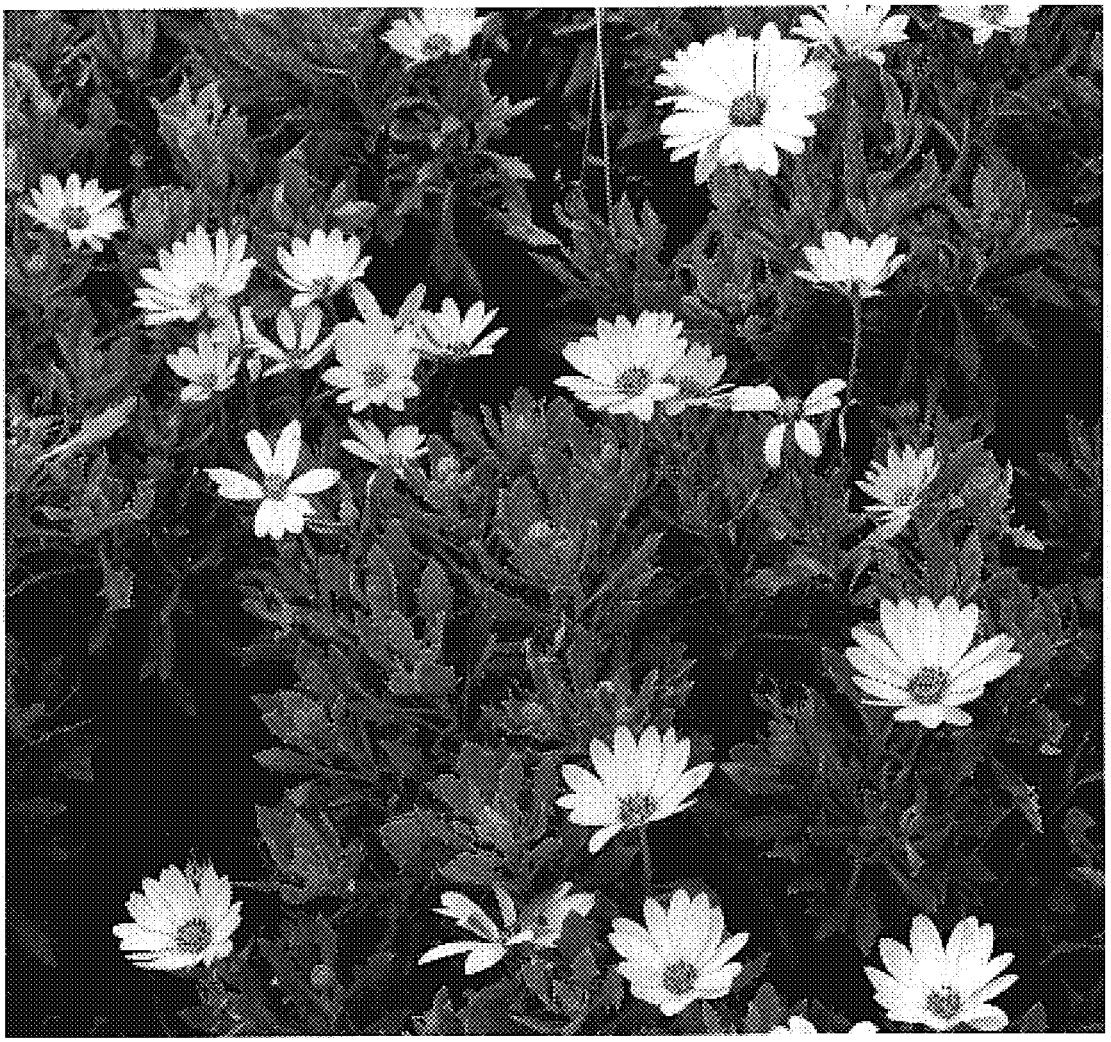

* * * * *